United States Patent [19]
Noble et al.

[11] Patent Number: 5,762,922
[45] Date of Patent: Jun. 9, 1998

[54] ANTIOXIDANTS AND INTRACELLULAR GLUTHATHIONE RAISING AGENTS FOR THERAPEUTIC TREATMENTS

[75] Inventors: Mark David Noble; Margot Mayer. both of London, England

[73] Assignee: Ludwig Institute for Cancer Research. New York, N.Y.

[21] Appl. No.: 270,059

[22] Filed: Jul. 1, 1994

Related U.S. Application Data

[63] Continuation-in-part of Ser. No. 189,474, Jan. 31, 1994.

[51] Int. Cl.$^6$ .......................... A61K 45/05; A61K 38/21
[52] U.S. Cl. .................. 424/85.4; 424/85.1; 530/351; 530/399
[58] Field of Search .................. 424/85.1, 85.4; 530/351, 399

[56] References Cited

U.S. PATENT DOCUMENTS 4,985,241  1/1991  Zimmerman et al. ................. 424/85.1

OTHER PUBLICATIONS

Johnson et al., Blood, vol. 73 (3), pp. 678–683, 1989.
Lanius et al., Neuroscience Letters, vol. 163, pp. 89–92 1993.
Weiss, Science, vol. 260, pp. 1072–1073, May 1993.
Lewis et al, Annals of New York Academy Sciences, vol. 692, pp. 201–208, 1993.
Lewis, Exp. Neurology, vol. 124(1), pp. 73–88, Nov. 1993.
Peristeris et al., Cell Immunol., vol. 140(2), pp. 390–399, 1992.
Selmaj et al., J. Clin Invest., vol. 87, pp. 949–954, 1991.
Hofman et al., J. Exp. Med., vol. 170, pp. 607–612, 1989.
Yang et al., J. Pediatrics, vol. 119(3), pp. 343–354, 1991.
Rothstein et al., Immunology Series, vol. 56, pp. 453–481, 1992.
Louis et al., Science, vol. 259, pp. 689–692, Jan. 1993.
T.-C. Chao et al., J. Leukocyte Biol., vol. 0, Suppl. 2, Annual Meeting Abstracts No. 139, p. 53, 1991.
Sugino et al., Biology of Reproduction, vol. 49, pp. 354–358, 1993.
Fiers et al., Immunology Letters, vol. 16, pp. 219–226, 1987.
Bone, Annals of Internal Medicine, vol. 115, pp. 457–469, 1991.

*Primary Examiner*—Chhaya D. Sayala
*Attorney, Agent, or Firm*—Klauber & Jackson

[57] ABSTRACT

The invention is directed to therapeutic methods for treating diseases associated with tumor necrosis factor-alpha (TNF-$\alpha$) induced cell toxicity and/or complement induced cell toxicity, improved methods for treating diseases whose therapy comprises the administration of at least one growth factor, and improved methods for preventing cell death associated with acute tissue injury.

12 Claims, 10 Drawing Sheets

FIG. 10

ANTIOXIDANTS AND INTRACELLULAR GLUTHATHIONE RAISING AGENTS FOR THERAPEUTIC TREATMENTS This application is a continuation-in-part of application Ser. No. 08/189,474, filed Jan. 31, 1994, now pending.

FIELD OF THE INVENTION

The invention is directed to therapeutic methods for treating diseases associated with tumor necrosis factor-alpha (TNF-α) induced cell toxicity and/or complement induced cell toxicity, improved methods for treating diseases whose therapy comprises the administration of at least one growth factor, and improved methods for preventing cell death associated with acute tissue injury.

BACKGROUND OF THE INVENTION

The abilities to prevent undesired cell death, and to promote the generation and survival of desired cells, are of considerable importance in present and future medical practice. For example, severe clinical problems are caused by death of oligodendrocytes in multiple sclerosis, death of neurons in diabetic neuropathy and in amyotrophic lateral sclerosis (ALS), death of kidney cells in a variety of kidney diseases, and death of pancreatic islet cells that leads to diabetes. Other examples of deficiencies that relate to the survival and/or the number of a particular kind of cell are the failure of patients to produce sufficient red blood cells, resulting in anemia.

It has become appreciated that two major environmental influences control the generation and survival of all cell types.

The first is the presence of toxic compounds. The environment of a cell can also cause cell death by the presence of substances injurious to cells. A variety of toxic compounds have been identified, but there are two of particular interest with respect to the present invention. The first of these is TNF-α, which is able to kill oligodendrocytes, the myelin-forming cells of the central nervous system (Louis, J. C., et al., *Science*, 259:689–692, (1993); Selmaj, K. W., et al., *Ann Neurol.* 23:339–346 (1988); Merrill, J. E., *Dev. Neurosci.* 13:130–137 (1991). TNF-α is though to be of particular importance in the pathogenesis of multiple sclerosis (MS), in which myelin is broken down and oligodendrocytes are killed (Matthews, W. B., *McAlpine's Multiple Sclerosis*, 2nd edition: Churchill Livingstone, London (1991)), and TNF-α has been found to be present in the sites of MS lesions (Hofman et al., *J. Exp. Med.* 170:607–616 (1989); Selmaj, et al., *J. Clin. Invest.* 87:949–953 (1991). TNF-α has also been associated with a number of other diseases including rheumatoid arthritis, for which experimental therapies with antibodies or other proteins that inactivate TNF-α have been proposed. TNF-α is also thought to contribute to cerebral malaria, endotoxic shock and to play a role in AIDS.

The second cytotoxic compound (or more accurately, collection of compounds) of particular interest in the present application is complement, a collection of proteins that when activated in a cascade, form channels in cells that can lead to cell death and tissue injury. Complement activation, and subsequent damage to cells, is thought to be of importance in autoimmune diseases, such as multiple sclerosis, rheumatoid arthritis or myasthenia gravis and in tissue injury following reperfusion. Complement-mediated injury of cells is also of serious consequences in storage of platelets for blood transfusion and identification of non-toxic compounds capable of inhibiting cell damage by complement could be of considerable importance in prolonging the usual half-life of platelet preparations.

It has been shown that at least some types of cell death caused by exposure to toxic substances can be prevented by the application of growth factors that stimulate receptor tyrosine kinase (RTKs) and RawTKs. For example, application of CNTF can interfere with the ability of TNF-α to kill oligodendrocytes (Louis et al., *Science* 259:68–692 (1993)), and appropriate growth factors also can protect neurons against glutamate and nitric oxide toxicity (Schubert, D., et al. *Proc. Natl. Acad. Sci. U.S.A.* 89:8264–8267 (1992); Maiese et al., *J. Neurosci.* 13:3034–3040, (1993)). The treatment for diseases associated with TNF-α induced toxicity and/or complement induced toxicity, however, have been less than satisfactory. Thus, there exists a need to treat disease conditions associated with these forms of cell toxicity more effectively.

The second environmental influence that controls the generation and survival of cells is the presence of growth factors. It is necessary that the environment of cells contains appropriate growth factors, also known as survival factors or trophic factors, to prevent cells from undergoing apoptosis. Thus far, the known growth factors are proteins that stimulate cell surface receptors, leading to activation of intracellular tyrosine kinases (which may be part of the receptor itself or which may bind to the receptor as a separate molecule). Receptor tyrosine kinases (RTKs) and receptors associated with tyrosine kinases (RawTKs) have been grouped into several classes of related molecules, according to their structural resemblance with one another. Examples of growth factors that stimulate members of different families of RTKs and RawTKs are nerve growth factor (NGF) which supports the survival of a variety of neurons, ciliary neurotrophic factor (CNTF) which supports the survival of a variety of neurons and of oligodendrocytes, epidermal growth factor (EGF) which supports the survival of kidney cells and stimulates the division of a wide range of cell types, insulin-like growth factor I (IGF-I) which supports the survival of a variety of cell types, and interferon-gamma (IFN), which supports the survival of oligodendrocytes and also regulates expression of major histocompatibility antigens.

It also is known that the application of growth factors can be successfully used to treat diseases characterized by an insufficiency of a particular cell type or types. For example, the growth factor erythropoeitin (EPO) is used to treat anemia associated with renal disease or with chemotherapy, and granululocyte-colony stimulating factor (G-CSF) and granulocyte-macrophage colony stimulating factor (GM-CSF) are used to treat neutropenia associated with chemotherapy. Related therapies currently are being explored for treatment of diseases of the nervous system. For example, clinical trials are currently being conducted with CNTF for the treatment of amyotrophic lateral sclerosis (ALS) and with nerve growth factor for the treatment of diabetes-associated neuropathy. The therapies, however, administer extremely high levels of the growth factor. Thus, there exists a need to discover adjuvant therapies that would increase the efficacy of growth factor action in promoting cell generation and/or survival and thus decrease the amount of a growth factor needed to yield a desired effect. As one of the major costs of disease treatment is the cost of recombinant growth factors, the discovery of compounds that increase the effectiveness of such factors could significantly reduce the costs associated with administration of the growth factors.

The inventors have unexpectedly discovered that compounds capable of raising intracellular glutathione levels such as NAC can be administered to treat diseases or conditions associated with TNF-α induced cell toxicity and/or complement-mediated cell toxicity and diseases or conditions whose therapy comprises the administration of at least one growth factor.

The inventors have also unexpectedly discovered that combinations of small molecules from within the family of antioxidants, such as NAC, Vitamin C, or trolox, combined with each other or in combination with progesterone, will support cell survival in the absence of any exogenous stimulator of receptor tyrosine kinase activity. Thus, these combinations of small molecules together form a suitable formulation for use in clinical conditions where it is desirable to prevent cell death, particularly cell death associated with acute tissue injury.

SUMMARY OF THE INVENTION

It is therefore an object of the present invention to provide therapeutic agents to treat diseases associated with TNF-α and/or complement induced cell toxicity. It is a further object of the invention to prevent undesired complement-mediated toxicity to cells in vitro.

It is yet a further object of this invention to provide therapeutic agents to treat diseases or conditions characterized by an insufficiency of a particular cell type or types and whose therapy comprises the administration of at least one growth factor to promote the survival of the particular cell type or cell types.

In accomplishing these and other objects, there is provided a method for treating a disease or condition associated with cell induced toxicity selected from the group consisting of TNF-α, complement, or TNF-α and complement induced cell toxicity, said method comprising administering to a patient suffering therefrom a therapeutically effective amount of an agent capable of raising intracellular glutathione levels.

In another aspect of the invention, there is provided a method for treating a disease or condition characterized by an insufficiency of a particular cell type or types and whose therapy comprises the administration of at least one growth factor to promote the survival of the particular cell type or cell types, said method comprising administering a therapeutically effective amount of said growth factor in combination with an agent capable of raising intracellular glutathione levels.

In yet another aspect of the invention, there is provided a method for treating a disease or condition characterized by an insufficiency of a particular cell type or types and whose therapy comprises the administration of CNTF to promote the survival of the particular cell type or cell types, the method comprising administering a therapeutically effective amount of CNTF in combination with an agent selected from the group consisting of vitamin C or trolox.

In yet a further aspect of the invention, there is provided a method for treating a disease or condition characterized by an insufficiency of a particular cell type or types and whose therapy comprises the administration of IGF-1 to promote the survival of the particular cell type or cell types, the method comprising administering a therapeutically effective amount of IGF-1 in combination with an agent selected from the group consisting of vitamin C or trolox.

In a further aspect of the invention, there is provided a method for preventing cell death associated with acute tissue injury, the method comprising administering a therapeutically effective amount of progesterone in combination with an agent selected from the group consisting of NAC, vitamin C, or trolox.

In yet another aspect of the invention, there is provided a method for preventing cell death associated with acute tissue injury, the method comprising administering a therapeutically effective amount of NAC in combination with an agent selected from the group consisting of vitamin C, or trolox.

In yet another aspect of the invention, there is provided a method for inhibiting cell damage caused by complement in vitro, said method comprising exposing said cell to an effective amount of an agent capable of raising intracellular glutathione levels.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2(B) shows the effects of N-acetyl-L-cysteine (NAC) and CNTF on.

DETAILED DESCRIPTION OF THE INVENTION

Glutathione is a tripeptide that is normally found in all animal cells and most plants and bacteria at relatively high (1–10 millimolar) concentrations, and helps to protect cells against oxidative damage that would otherwise be caused by free radicals and reactive oxidative intermediates (ROIs) produced during cell metabolism or as the results of, for example, drug overdose. Glutathione is itself the major scavenger of reactive oxidative intermediates present in all eukaryotic forms of life and is generally required to protect cells against damage by oxidants. Glutathione reduces (and thereby detoxifies) intracellular oxidants and is consumed by this reaction. Glutathione is oxidized to the disulfide linked dimer (GSSG), which is actively pumped out of cells and becomes largely unavailable for reconversion to reduced glutathione. Thus, unless glutathione is resynthesized through other pathways, utilization of this compound is associated with a reduction in the amount of glutathione available.

As well as being able to interact directly with ROIs to eliminate these damaging reactive species, the antioxidant effects of glutathione are also mediated less directly by the role of this compound in maintaining such other antioxidants as ascorbate and α-tocopherol in reduced form. Thus, pharmaceutical compounds which elevate glutathione levels work, at least in part, through enhancement of the defense mechanisms seemingly utilized to normally protect tissue from ROI mediated damage.

The inventors have discovered that compounds capable of raising intracellular glutathione levels can be administered to treat diseases or conditions associated with TNF-α induced and/or complement-induced cell toxicity and can be used to protect cells in vitro from TNF-α induced and/or complement-induced cell toxicity. The inventors have also discovered that compounds capable of raising intracellular glutathione levels can be administered to treat more effectively diseases or conditions characterized by an insufficiency of a particular cell type or types and whose therapy comprises the administration of at least one growth factor to promote the survival of the particular cell type or cell types.

Compounds capable of raising intracellular glutathione levels are known in the art and include N-acetylcysteine (NAC), L-2-oxothizolidine-4-carboxylic acid (Meister et al., *J. Am. Coll. Nutri.*, 5:137–151 (1986)). GSH-esters (Anderson, M. E., et al., *Anal. Biochiem.*, 183:16–20 (1989)) and glutathione itself (Vina, J., et al., *Br. J. Nitr.*, 62:683–691 (1989)).

A preferred compound of the present invention capable of raising intracellular glutathione levels is NAC, an extensively documented compound. (Taniguchi, N., et al., *Glutathione Centennial: Molecular Properties and Clinical Implications Academic*, New York (1989); Meister, A., et al., *J. Am. Coll. Nutri.*, 5:137–151 (1986); Aruoma, O. I., et al., *Free Radical Biol. Med.*, 6:593–597 (1989); and Burgunder, J. M., et al., *Eur. J. Clin. Pharmacol.*, 36:127–131 (1989)). NAC has been routinely used in humans to replenish glutathione following acetaminophen overdose (which leads to a fatal depletion of glutathione in the liver) and in treatment of pulmonary disorders (Aruoma, O. I., et al., *Free Radical Biol. Med.*, 6:593–597 (1989); Burgunder, J. M., et al., *Eur. J. Clin. Pharmacol.*, 36:127–31 (1989); Smilkstein, M. J., et al., *Engi. J. Med.* 319:1557–1562 (1988); Holdiness, M. R., *Clin. Pharmacokiner*, 20:123–134 (1991); Moldeus, P., et al. *Respiration* 50: Suppl. 1 pgs. 31–42; Olsson, B., et al., *Eur. J. Clin. Pharmacol.*, 34:77–82 (1988) and Ventresca, G. P., et al. In:*Drugs in Bronchial Mycology*, eds. Braga, P. C. and Allegra, L.: Raven, New York, pp. 77–102 (1989)). This non-toxic drug enters cells readily and replenishes the intracellular cysteine required to produce glutathione, thus leading to an increase in glutathione levels. NAC also reacts directly with ROIs, thus protecting cells against these toxic compounds. This twofold action of NAC places this compound in a wholly different class from other ROI scavengers such as superoxide dismutase, catalase, ascorbate, and α-tocopherol which do not enhance cellular production of glutathione.

Diseases associated with TNF-α and complement induced cell toxicity include multiple sclerosis and rheumatoid arthritis. In the former case, TNF-α and complement may be directly toxic to oligodendrocytes. In the latter case, it is not yet known precisely how TNF-α and complement contribute to cartilage destruction and local inflammation. Diseases associated with TNF-α induced cell toxicity include cerebral malaria, endotoxic shock, and AIDS. Diseases associated with complement induced cell toxicity include autoimmune diseases, such as multiple sclerosis, myasthenia gravis, some forms of diabetes, and immune glomerular injury following burn injury and in tissue injury following reperfusion.

Compounds which increase intracellular glutathione presumably prevent the cytotoxic effects of TNF-α by preventing expression or activation of genes involved in causing cell death. The mechanism by which these compounds prevent complement-mediated death may be by blocking damage caused by production of reactive oxidative intermediates.

In a preferred embodiment of the invention, the invention comprises administering NAC solely or in combination with a growth factor such as CNTF or IGF-I to treat MS.

Compounds that raise intracellular glutathione levels also can be used to treat diseases or conditions characterized by an insufficiency of a particular cell type or types and whose therapy comprises the administration of at least one growth factor to promote the generation and/or survival of the particular cell type or cell types. The compounds that raise intracellular glutathione levels increase the efficacy of the growth factor action in promoting cell generation and/or survival and thus decrease the amount of growth factor needed to yield the desired effect. The specific growth factor to be used is decided on a disease-specific basis utilizing knowledge known in the art.

For example, in diabetes patients being treated with NGF for diabetic neuropathy, those patients would also be treated with a compound capable of elevating intracellular glutathione levels. For patients being treated with CNTF, brain derived neurotrophic factor, basic fibroblast factor, or combinations thereof for ALS, those patients would also be treated with a compound capable of elevating intracellular glutathione levels. Similarly for Parkinson patients and Alzheimer's patients being treated with glial derived neurotrophic factor and/or nerve growth factor (and related family members such as neurotrophin-3 and neurotrophin-4), respectively, those patients would also be treated with a compound capable of elevating intracellular glutathione levels. In a preferred embodiment, the compound that raises intracellular glutathione levels is NAC.

Additionally, patients with anemia associated with chemotherapy or renal failure are commonly treated with erythropoetin (EPO), and patients with neutropenia are treated with granulocyte-colony stimulating factor (G-CSF) and granulocyte-macrophage colony stimulating factor (GM-CSF). In the aforementioned therapies, the amount of growth factor administered can be decreased by the concomitant administration of a compound that raises intracellular glutathione levels, preferably NAC.

In another embodiment, antioxidants such as Vitamin C or Trolox also can be used to treat diseases or conditions characterized by an insufficiency of a particular cell type or types and whose therapy comprises the administration of at least one growth factor to promote the generation and/or survival of the particular cell type or cell types. The antioxidants increase the efficacy of the growth factor action in promoting cell generation and/or survival and thus decrease the amount of growth factor needed to yield the desired effect. In a preferred embodiment, the disease or condition is amyotrophic lateral sclerosis, the growth factor is CNTF, and the antioxidant is either Vitamin C or Trolox.

The inventors have also discovered that cell death associated with acute tissue injury, such as CNS trauma which includes spinal injury, stroke, surgery, hypoxia, reperfusion injury, kidney failure, acute liver failure, septic shock, infarction, embolism, and necrosis induced by bacteria, viruses or other organisms can be prevented by the administration of combinations of antioxidants, such as NAC, Vitamin C, or Trolox, or combinations of antioxidants, such as NAC, Vitamin C, or Trolox, with progesterone. Thus, one embodiment of this invention is the use of cocktails of compounds in the prevention of cell death associated with acute tissue injury, in which the cocktail contains either a combination of antioxidants, of which at least one is an agent capable of raising intracellular glutathione levels, or a combination of one or more antioxidants with progesterone, or a combination of at least one member from the following three groups of progesterone, a compound capable of raising intracellular glutathione levels, and another antioxidant. Preferred antioxidants include NAC, trolox, and Vitamin C. A preferred agent capable of raising intracellular glutathione levels is NAC. The cocktails may also be used to prevent cell death associated with chronic cell death syndromes, such as Parkinson's disease, ALS, Alzheimer's, and muscular dystrophy. These syndromes are believed to stem from apoptic states.

The treatment of the patient may be with the compounds of the present invention or their salts. Such salts include salts with pharmacologically acceptable cations including, e.g., alkaline or alkaline-earth metals, specifically sodium, potassium or calcium, or salts with physiologically acceptable bases, e.g., simple amines Such as ammonia, and in particular with basic amino acids such as lysine, arginine and the like. Preferred compounds are NAC and its salts.

The compounds of the present invention may be formulated in a variety of ways. These include but are not limited to: solid forms, such as powders, granulates, tablets, capsules, dragees; liquid forms such as sterile injectable solutions, solutions or suspensions for oral administration; suppositories; aerosols; and topical or ingestible slow-release formulations. The formulations may include conventional additives, such as flavoring, excipients, stabilizers, effervescent agents, antioxidants, or the like. These additives will be used in conventional amounts and, with the exception of excipients, will usually be present in a total amount of less than about 10 wt. %. For slow release particles, various physiologically acceptable biologically degradable polymers may be employed, such as polylactates, polyglycolates, polyaldehydes, polyanhydrides, and the like.

Liposomes may also be employed as carriers, wherein the compounds of the present invention are present in the lumen of the liposome. Preparation of liposomes is conventional and is extensively described in the literature, and need not be described here. In a preferred embodiment, the concentration of the NAC compound in the liposome lumen will generally be in the range of from about 0.01 mM to about 10 mM. The particle size of the liposomes will generally be in the range of about 1 to 500 micron. A further improvement in delivery of the therapeutic agent can be achieved, for those diseases where the disease is associated with specific cells, by conjugating to the liposomes molecules which provide for specific targeting. For example, antibodies may be bound to the liposome, either covalently or noncovalently, where the antibodies may be specific for oligodendrocytes, spinal ganglion neurons, chondrocytes or kidney cells.

Any convenient mode of administration of the compounds of the present invention may be employed. Administration may be oral, parenteral, via an enema, topical, or the like, such as by injection, oral tablet or powder solutions or other convenient means. Oral administration is preferred. Administration may be daily, multiple dosages per day, bidaily, or any other convenient period.

The compounds of the present invention are administered in an amount sufficient to treat the disease. An amount adequate to accomplish this is defined as a "therapeutically effective amount" or "efficacious amount". Amounts effective for this use will depend upon the severity of the condition, the general state of the patient, the route of administration, and other factors known to those skilled in the art. For example, the doses of the compound that raises intracellular glutathione levels, preferably NAC, could range from 100 mg to 10 grams daily, depending on the severity of disease and specificities of treatment, and whether the compound that raises intracellular glutathione levels is administered in combination with a growth factor. Doses for other antioxidants, such as Vitamin C or Trolox would be in the same range as for NAC. Doses for progesterone would be according to standard clinical usage well known in the art.

In a number of experiments directed to the identification of compounds that can protect cells against exposure to noxious stimuli, i.e., TNF-α, glutamate, and complement, and exposure to an insufficient activity of endogenous growth factors, NAC prevented glutamate induced death of oligodendrocytes and TNF-α induced death of oligodendrocytes and L929 fibroblasts. NAC also protected oligodendrocytes against complement-induced death. Ciliary neurotrophic factor (CNTF) also provided some protection for oligodendrocytes against TNF-α induced death, but was less effective than NAC. However, suboptimal doses of NAC and CNTF acted synergistically to protect oligodendrocytes against TNF-α induced death, as did suboptimal doses of NAC+IGF-I.

In apoptosis models, NAC markedly enhanced the extent of oligodendrocyte survival obtained with suboptimal concentrations of CNTF or IGF-I and of spinal ganglion neuron survival obtained with suboptimal concentrations of nerve growth factor. A further example of the ability of NAC to enhance response of cells to tyrosine kinase stimulators was seen with PDGF, for which NAC enhanced the production of 0-2A progenitors and oligodendrocytes in response to stimulation with this growth factor.

The examples thus demonstrate that NAC enhances the effectiveness of at least one family member from amongst most major families of the proteins causing activation of RTKs and RawTKs. Specifically, the examples show that the effectiveness of epidermal growth factor (EGF), platelet-derived growth factor (PDGF), insulin-like growth factor-I (IGF-I), ciliary neurotrophic factor (CNTF) and interferon-gamma (IFN) are all enhanced in experiments designed to examine known activities of these compounds. All of these compounds act through stimulation of tyrosine kinase activity, which EGF, PDGF and IGF-I binding to proteins with intrinsic tyrosine kinase activity (RTKs; see, e.g., Chao, Neuron 9:583–593, 1992 for review) and CNTF and IFN binding to proteins that associate with tyrosine kinases (RawTKs; Gearing, et al., Science 255:1434–1437 (1992); Ip, et al., Cell 69:1121–1132 (1992)).

Prior to the data described in this invention, it was widely perceived that the promotion of cell survival would require the activation of RTKs and/or RawTKs. It has been unexpectedly discovered, however, that appropriate combinations of compounds that do not work through these pathways will also promote cell survival. Examples III(H) and III(J) demonstrate the ability of progesterone plus NAC, Trolox or Vitamin C to support oligodendrocyte survival in the absence of RTK or RawTK stimulators. The presence of NAC plus Trolox or Vitamin C has similar effects (Example III(I), and the combination of progesterone, NAC and Trolox or Vitamin C (Example III(J)) is a particularly effective promoter of cell survival in the absence of stimulators of RTK or RawTK agonists.

Oligodendrocytes were chosen for a number of the examples because they provide an excellent model for the functioning of cells in vivo. Indeed, the applicability of the in vitro oligodendrocyte model to the patient treatment was confirmed by an experiment which demonstrated that treating a patient in the advanced stages of MS with NAC resulted in significant gains.

The following examples are offered by way of illustration and not by way of limitation.

EXAMPLE I

A. Preparation of Oligodendrocyte Cultures

Purified oligodendrocytes were generated from cultures of O-2A progenitors derived from 7 day old rats and purified using a specific antibody-capture methodology (Wysocki, L. J., et al., Proc. Natl. Acad. Sci. U.S.A. 75:2844–2848 (1978)) (the contents of which are incorporated herein by reference). Single cell suspensions were prepared as described in (Mayer, M., et al., Glia 8:12–19 (1993)) (the contents of which are incorporated herein by reference).

Purified cells were grown on poly-L-lysine coated glass coverslips in Dulbecco's modified Eagle's medium (DMEM) supplemented with 25 µg/ml gentamicin, 2 mM-glutamine, 1 µg/ml bovine pancreas insulin, 100 µg/ml human transferrin, 0.0286% (v/v) BSA pathocyte, 0.2 µM-progesterone, 0.10 µM-putrescine, 0.45 µM L-thyroxine, 0.224 µM-selenium and 0.49 µM 3,3',5-triiodo-L thyroxine; modified from Bottenstein and Sata (Bottensteine, J. E., et al., Proc. Natl. Acad. Sci. U.S.A. 76:514–517, (1979) (the contents of which are incorporated herein by reference).

The 0-2A progenitor purification protocol was modified from that previously adapted to the 0-2A lineage (Barres, B. A., et al., Cell 70:31–46 (1992)) (the contents of which are incorporated herein by reference), using a negative selection with the Ran-2 antibody (Bartlett, P. F., et al. Brain Res. 204:339–351 (1981)) to eliminate type-1 astrocytes, followed by anti-GalC antibody (Ranscht, B., et al. Pro. Natl. Acad. Sci. U.S.A. 79:2709–2713 (1982) treatment to remove oligodendrocytes. The specific antibody phenotype of 0-2A progenitors (A2B5±/GalC-) allows purification of these cells from the remaining cell suspension. The suspension was plated on an A2B5 antibody coated dish (Eisenbarth, et al., Proc. Natl. Acad. Sci. U.S.A. 76:4913–4916 (1979)) to allow binding of all A2B5+ cells to the plate. The supernatant was removed and the plate was washed with DMEM-BS. Cells were allowed to bind to the specific plates for 20–30 minutes in an incubator at a temperature of 37° C. This procedure yielded $2 \times 10^5$ 0-2A progenitor cells from an initial $2 \times 10^6$ mixed cell culture from a rat optic nerve. The bound cells were removed by gentle scraping and washing, and plated on PLL-coated coverslips in a 24 well plate. After the cells were allowed to adhere for 1 hr, 300 ul of DMEM-BS was added and the cells were grown for 3 days. DMEM-BS induces differentiation of all cells into oligodendrocytes (Raff, M. C., et al., Nature 303:390–396 (1983)). By staining parallel coverslips with oligodendrocyte-specific antibodies (see below), it was confirmed that 100% of the cells in such cultures were oligodendrocytes. In the final culture the number of contaminating A2B5-negative cells (type-1 astrocytes and oligodendrocytes) represented <0.5% of the total cells while 0-2A progenitors were present at <99.5–100%. Antibodies for coating the plates were used at the following concentrations: anti-Ran-2 [2.5 µg/ml], anti-GalC [2.5 µg/ml], A2B5 antibody [5 µg/ml].

B. Preparation of Embryonic Sensory Neuron Cultures

Cultures of embryonic sensory neurons were generated by dissecting the spinal ganglia of 16 day old rat embryos, dissociating cells to a single cell suspension by standard techniques (e.g., Groves, et al. Dev. Biol. 159:87–104 (1993)) (the contents of which are incorporated herein by reference) and treated with 04 antibody+complement to kill Schwann cells (Sommer et al. Dev. Biol. 83:311–327 (1981); Jessen et al. Glia 4:195–204 (1991)). The remaining cells, the majority of which appeared to be fibroblast-like cells, were plated onto fibronectin-coated coverslips or PLL-coated coverslips at a density of 1000 total cells/cover slip.

C. Preparation of L929 Fibroblasts L929 fibroblasts were maintained in flasks in DMEM containing 10% fetal calf serum (FCS). Prior to assays, cells were plated in 96-well plates at a density of 30,000 cells per well in DMEM-FCS.

EXAMPLE II

A. Response of L929 Fibroblasts to TNF-α+NAC

L929 fibroblasts prepared according to Example I(c) were plated in 96-well plates at a density of 30,000 cells per well in DMEM-FCS. TNF-α (2ng/ml)±NAC was added after cells had settled. Twenty-four hours later the cells were analyzed using a standard MTT system and counted on a plate reader; within the range of cell densities tested there was a linear relationship between cell number and MTT labeling.

Figure 1A:
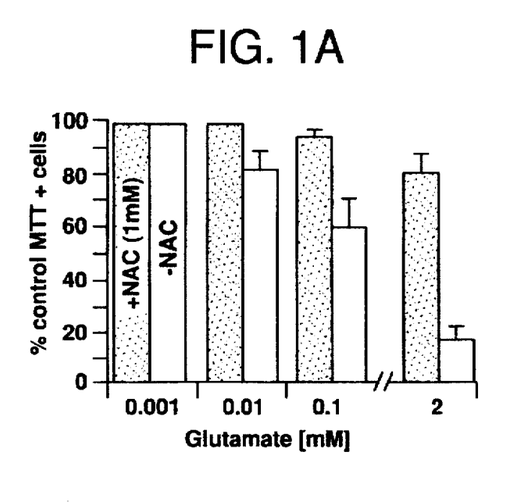
FIGS. 1(A)–(C) show the effects of various agents capable of raising intracellular glutathione levels on TNF-α and glutamate induced cell toxicity.
Figure 1B:
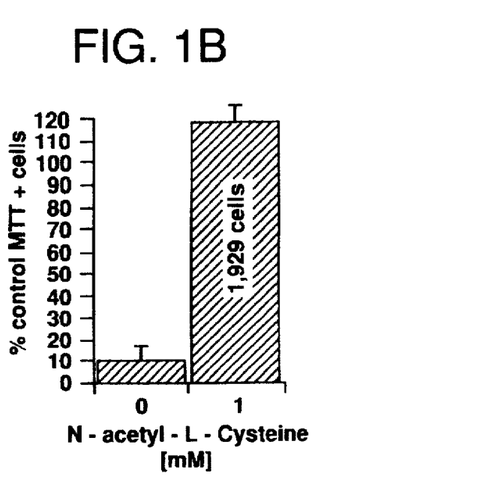

As shown in FIG. 1(B), cultures exposed to TNF-α without NAC contained almost no living cells. In contrast, cultures exposed to TNF-α+1 mM NAC showed no signs of extensive cell death. Thus, NAC prevented TNF-α mediated killing of L929 fibroblasts, a cell line highly sensitive to TNF-α-induced apoptosis.

The ordinate of FIG. 1(B) represents percentage of absorption values obtained as compared with cultures not treated with TNF-α. Values shown are means±SD for quadruplicate wells from one of two experiments, both of which yielded similar results. (Control values (100%)—MTT absorption of 1.17.)

B. Response of oligodendrocvtes to Glutamate+NAC

Purified oligodendrocyte-type-2 astrocyte (0-2A) progenitors prepared according to Example I(A) were plated onto PLL-coated coverslips.

The oligodendrocytes were then exposed to glutamate±NAC (single application for both compounds) at the concentrations indicated in FIG. 1(A) for 1 day before cultures were stained with MTT for 1 hour and examined under the light microscope (Mayer, M., et al. Glia 8:12–19 (1993); Mosmann, T., J. Immunol Meth. 65:55–63 (1983)); parallel cultures stained with anti-galactocerbroside antibodies (Ranscht, B., et al. Proc. Natl. Acad. Sci. U.S.A. 79:2709–2713 (1982)) always consisted of 100% oligodendrocytes.

As shown in FIG. 1(A), NAC protected oligodendrocytes against glutamate-induced cell death. Glutamate was cytotoxic for purified oligodendrocytes within 24 h within concentrations ranging from 10 µM to 2 mM. Cultures exposed to 100 or 200 µM glutamate for 24 hours showed a 50% reduction in the number of live oligodendrocytes, and cultures exposed to 2 mM glutamate showed a <85% reduction in cell number.

In contrast, cultures exposed to up to 200 µM glutamate in the presence of 1 mM NAC did not show any reduction in the numbers of live oligodendrocytes, and cultures exposed to 2 mM glutamate+1 mM NAC exhibited only a slight fall in cell number.

Growth of oligodendrocytes in the presence of NAC was associated with increases in the levels of intracellular glutathione. Cells grown in control medium contained 27 ng glutathione/ug of protein, as compared with 75 and 181 ng/μg protein for cells grown in the presence of 1 mM NAC for 7 or 15 hours, respectively.

In FIG. 1(A), the ordinate axis shows the % of cells that were alive (i.e., were MTT +) as compared with cultures that were not exposed at all to glutamate. There was an excellent correlation between MTT-positivity and cell survival as analyzed exclusively by morphology. The results shown are means± SEM of two experiments containing 8 replicates for each condition. Control values (100%)=403±42 cells.

C. Comparison of the Response of NAC, L-cysteine, L-cysteine-S-sulphate, and L-Cystine treated Oligodendrocytes to TNF-α

Oligodendrocytes prepared according to Example I(C) were plated on 96 well plates at a density of 3,000 cells/coverslip. After differentiation, oligodendrocytes were exposed for 3 days to 10 ng/ml TNF-α and various concentrations of the compounds indicated in FIGS. 1(C) to 1(G) before being analyzed as in Example II(B).

As shown in FIGS. 1(C) to 1(G), NAC protected oligodendrocytes against cell death induced by exposure to 10 ng/ml (TNF)-α, a dose that yielded a plateau killing of 50–60% of unprotected oligodendrocytes over 3 days (FIG. 1A, dose-response for TNF-α not shown). Significant protection against TNF-α mediated killing was conferred by 0.1 mM NAC and complete protection by 1 mM NAC (FIG. 1C). 1 mM NAC afforded similar protection against 50 ng/ml TNF-α, the maximal concentration examined (data not shown).

In FIGS. 1(C) to 1(G), the ordinate axis shows the % of cells that were alive (i.e., were MTT+) as compared with cultures that were not exposed at all to TNF-α. Values shown are means±SD for quadruplicate coverslips from one experiment; experiments with NAC were repeated 10 times with similar results, while experiments with other compounds were repeated twice. Control values (100%)=778±10 cells.

D. Response of Oligodendrocytes to TNF-α±NAC and±CNTF

Cultures of purified oligodendrocytes were prepared as in Example II(B). Oligodendrocytes were exposed for 3 days to TNF-α (10 ng/ml)±the indicated doses of (CNTF)±NAC.

Figure 1C:
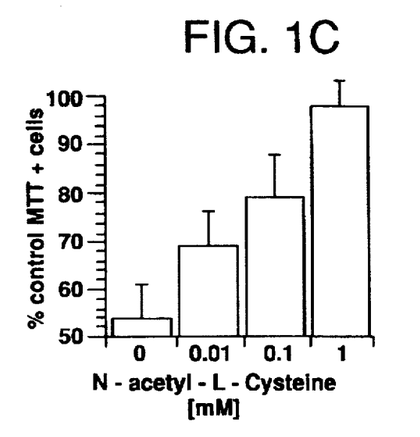
Figure 1D:
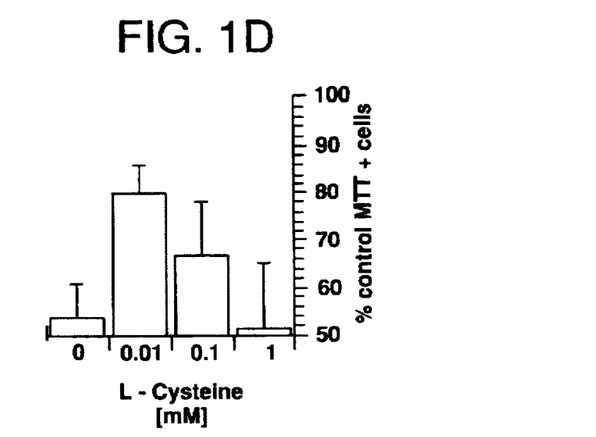
Figure 1E:
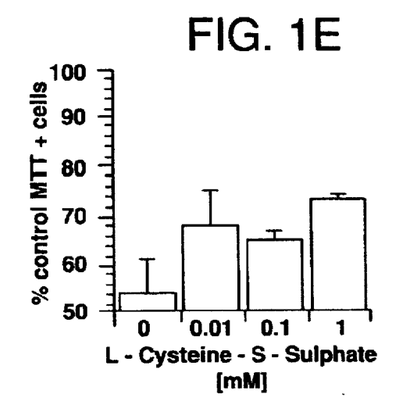
Figure 1F:
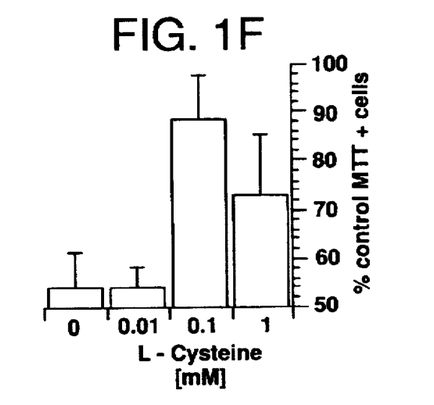
Figure 1G:
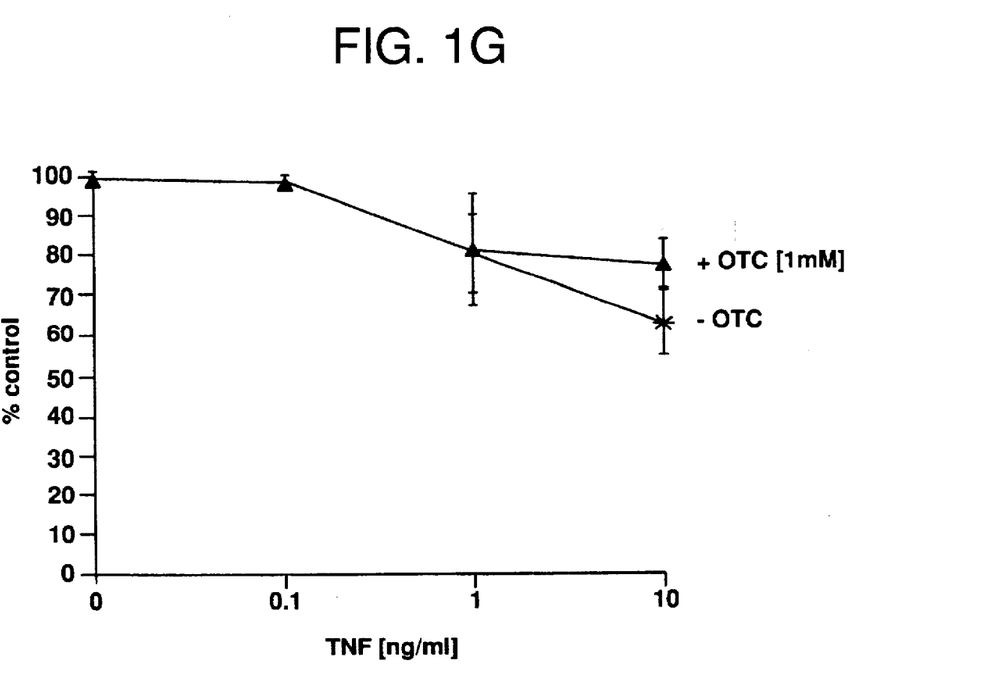
Figure 2A:
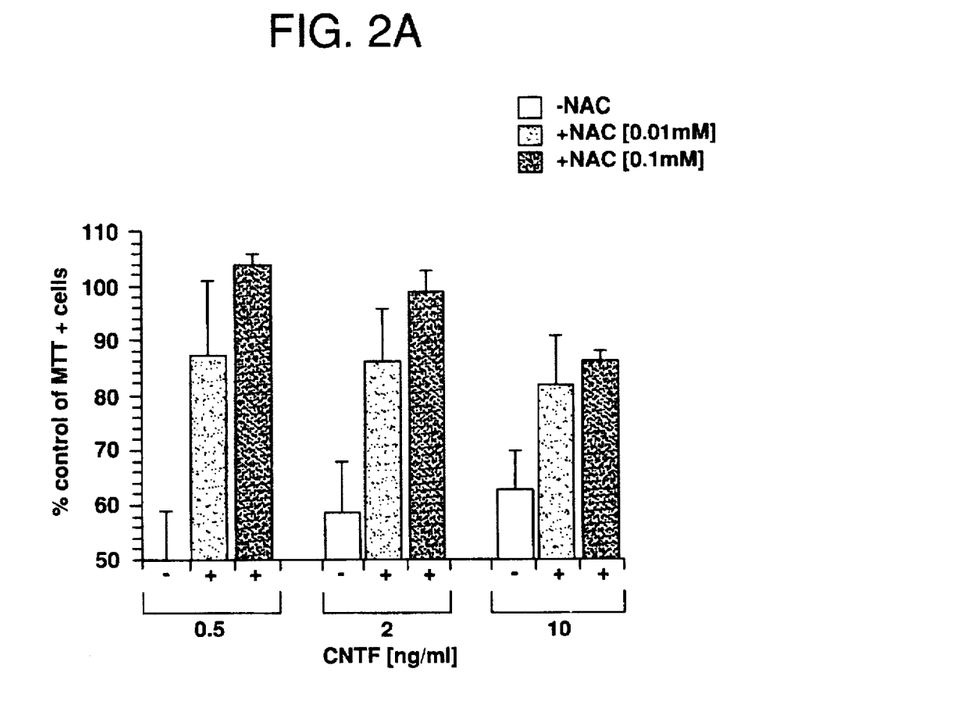
FIG. 2(A) shows the effects of N-acetyl-L-cysteine (NAC) and CNTF on TNF-α induced cell toxicity.

As shown in FIG. 2(A), CNTF did not protect cells as well as even 0.1 mM NAC (compare FIG. 1(C) with FIG. 2A), even at CNTF doses of up to 50 ng/ml. A striking synergy was exhibited between these compounds, however, in that cultures exposed to 0.5 ng/ml CNTF+0.01 mM or 0.1 mM NAC contained significantly more live oligodendrocytes than those exposed to NAC alone (see FIG. 1(C)) or to 0.5 ng/ml CNTF alone (which had no significant effect on survival). At higher doses of CNTF, the combined effect of the two compounds appeared to be additive. No doses of CNTF tested (up to 50 ng/ml, data not shown) rescued more than 26% of the population that was killed by TNF-α.

Values shown are means±SD for quadruplicate coverslips from one of four experiments, all of which yielded similar results. Control values (100%)=275±30 cells.

E. Comparison of the Response of Oligodendrocytes to Glutamate±NAC and±CNTF

Figure 2B:
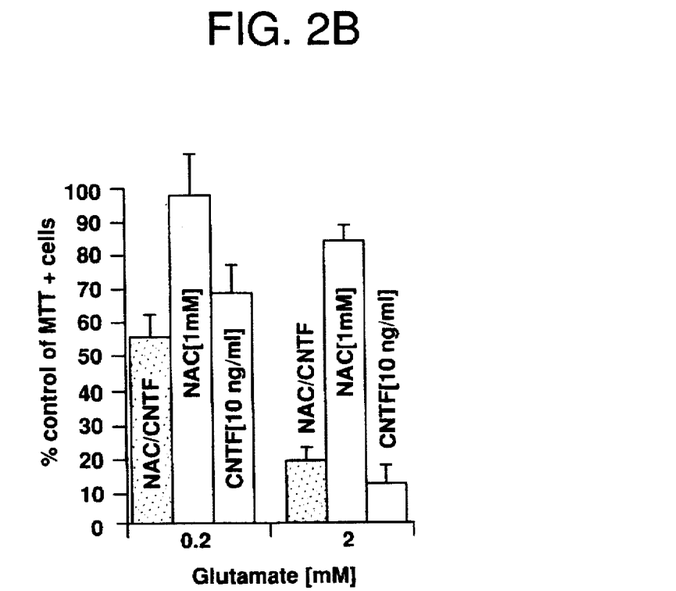
Figure 3:
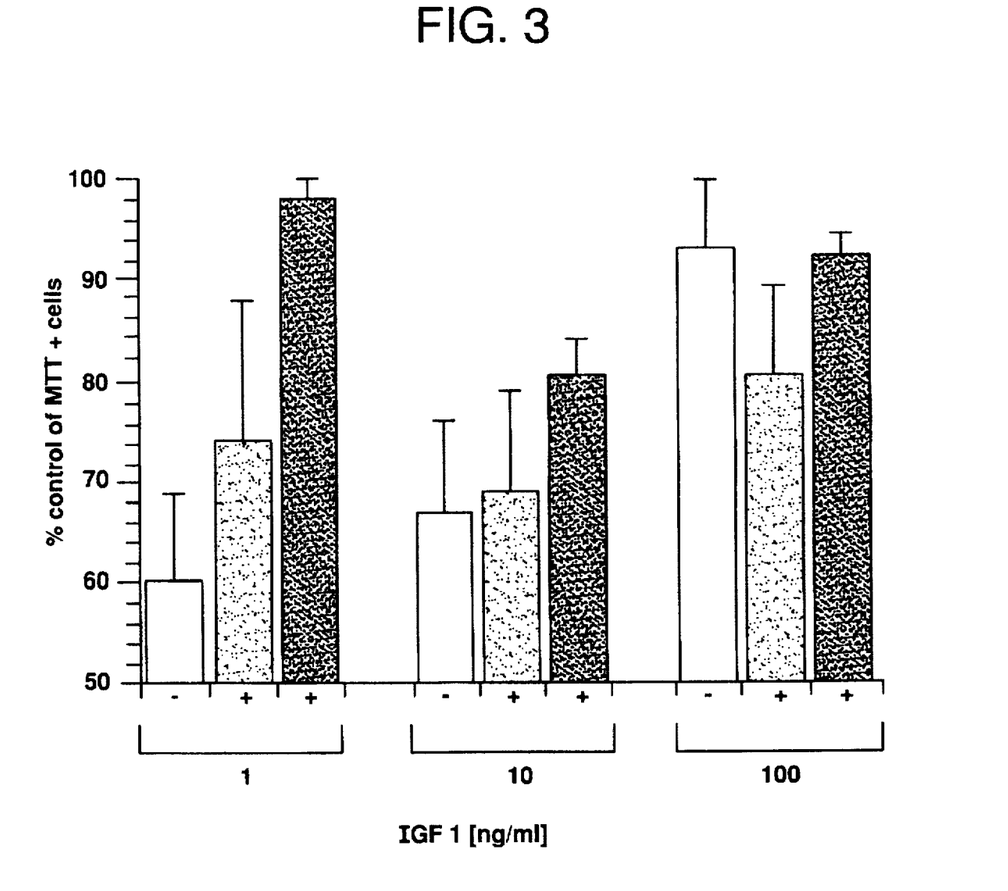
FIG. 3 shows the effects of NAC and IGF-I on TNF-α induced cell toxicity.

Cultures of purified oligodendrocytes were prepared as in Example II(B), and were exposed to glutamate±NAC or CNTF for 1 day before MTT labeling. As shown in FIG. 2(B), CNTF did not confer protection against glutamate-mediated killing at the dose shown, nor at lower doses (data not shown).

Apparently, the mechanism(s) by which CNTF protected oligodendrocytes from death in this Example and Example II(D) must have been at least in some manner different from NAC, since CNTF did not protect these cells against glutamate induced death.

Values shown are means±SD for quadruplicate coverslips from one of three experiments, all of which yielded similar results. Control values (100%)=640±84 cells.

F. Comparison of the Response of Oligodendrocytes to TNF-α±NAC and±IGF-I

Cultures of purified oligodendrocytes were prepared as in Example II(B). Cells were exposed for 3 days to TNF-α (10 ng/ml)±the indicated doses of IGF-I±NAC. For low doses of IGF-I, the presence of IGF-I+NAC led to a greater rescue than would be expected by a simple additive interaction between these two compounds. Values shown are means±SD for quadruplicate coverslips from one of four experiments, all of which yielded similar results.

EXAMPLE III

A. Rescue of Oligodendrocytes from Apoptosis by CNTF or IGF-I+NAC

Purified O-2A progenitors purified according to Example I(A) were plated at 2,500 cells/coverslip. After 3 days of growth in DMEM-BS, the resulting cultures of pure oligodendrocytes were switched to DMEM alone, a condition that induces apoptosis unless cells are exposed to appropriate growth factors. Cultures of oligodendrocytes received various concentrations of CNTF or IGF-1±1 mM NAC. After 3 further days of in vitro growth, cultures were analyzed in the same manner as experiments examining oligodendrocyte death induced by exposure to toxic stimuli. (See Example II(B))

Figure 4A:
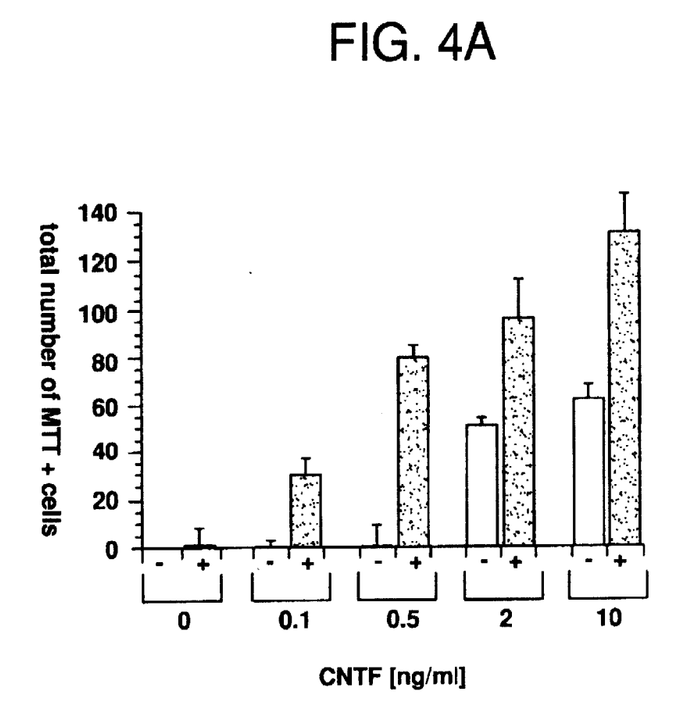
FIG. 4(A) shows the effects of NAC and CNTF on cells that would otherwise undergo apoptosis.
Figure 4B:
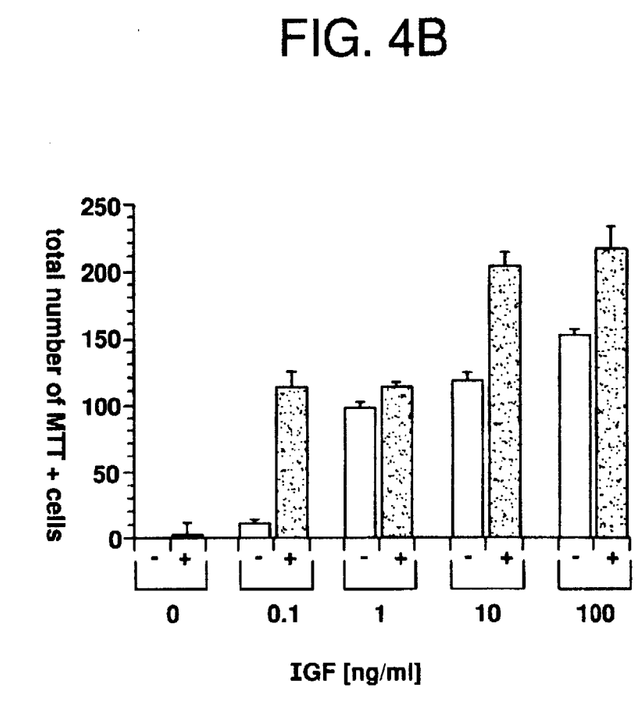
FIG. 4(B) shows the effects of NAC and IGP-I

As demonstrated in FIGS. 4(A) and (B), NAC alone did not promote cell survival, but the presence of 1 mM NAC was associated with significant increases in the extent of survival observed with either CNTF or IGF-1 applied by themselves. Values shown are means±SD for quadruplicate coverslips from one of four experiments, all of which yielded similar results.

B. Rescue of Oligodendrocytes from Apoptosis by INF or IGF+NAC

Figure 5:
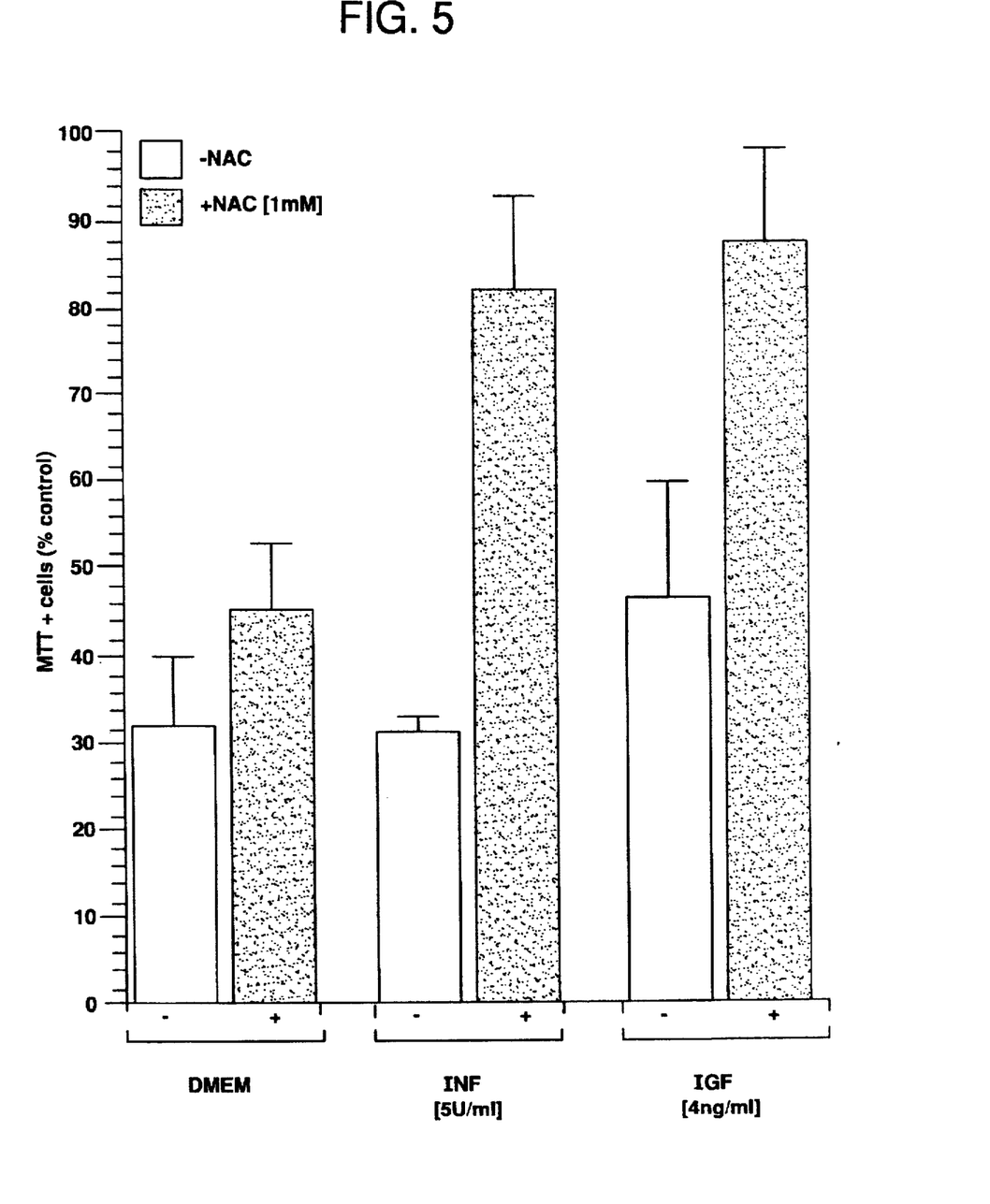
FIG. 5 shows the effects of NAC, IFN-gamma, and IGF-I on cells that would otherwise undergo apoptosis.

Purified O-2A progenitors purified according to Example I(A) were plated at 2,500 cells/coverslip. After 3 days of growth in DMEM-BS, the resulting cultures of pure oligodendrocytes were switched to DMEM alone, a condition that induces apoptosis unless cells are exposed to appropriate growth factors. Cultures of oligodendrocytes received various concentrations of IFN-gamma and IGF-I±1 mM NAC. After 3 further days of in vitro growth, cultures were analyzed in the same manner as experiments examining oligodendrocyte death induced by exposure to toxic stimuli. (See Example II(B)) As demonstrated in FIG. 5, NAC alone did not promote cell survival, but the combination of 1 mM NAC with either INF of IGF was associated with significant increases in the extent of survival observed with either INF or IGF applied by themselves.

Values shown are means±SD for quadruplicate coverslips from one of four experiments, all of which yielded similar results.

C. Rescue of Embryonic Sensory Neurons from Apoptosis by NGF+NAC

Figure 6:
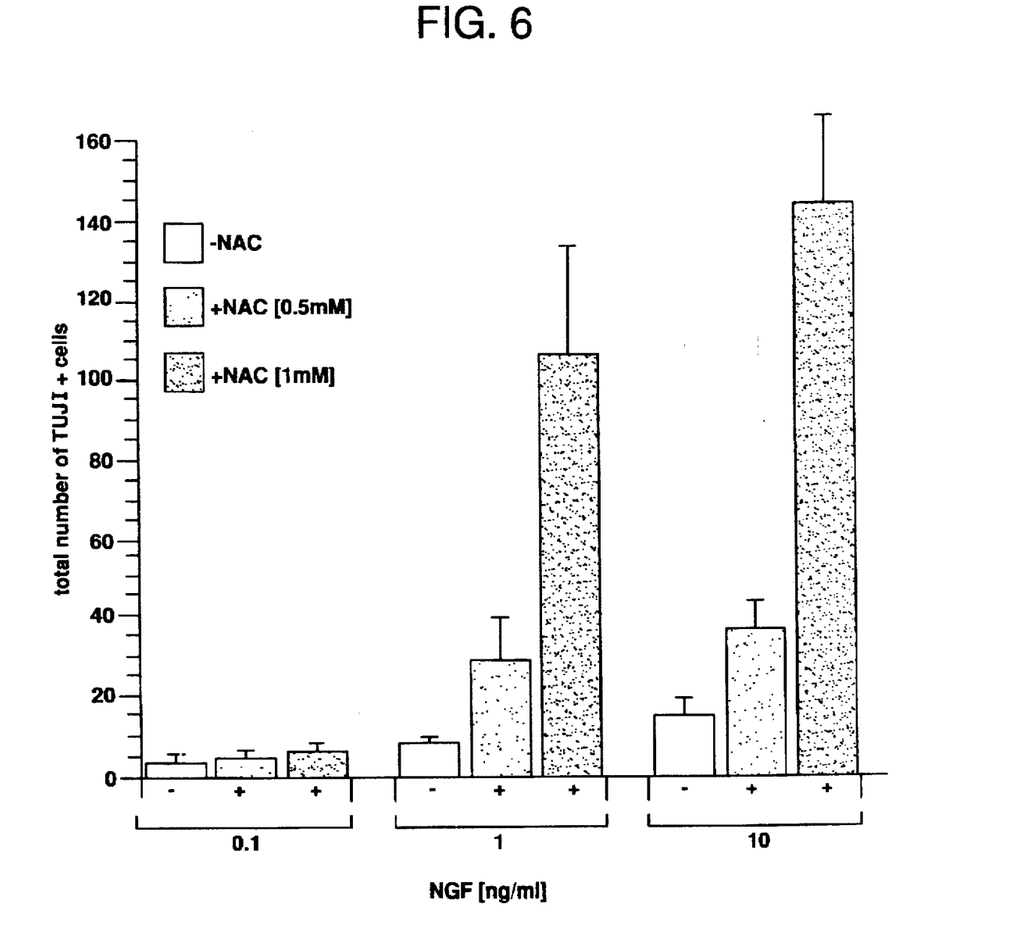
FIG. 6 shows the effects of NAC and nerve growth factor (NGF) on cells that would otherwise undergo apoptosis.

Cultures of embryonic sensory neurons were generated according to Example I(B). The cells were exposed to sub-optimal doses of NGF. As shown in FIG. 6, cultures exposed to NAC and either 1 or 10 ng/ml NGF on days 1 and 2 and labelled on day 3 contained 300–1000% more neurons than those exposed to NGF alone, depending upon the concentrations of NAC and NGF applied.

Neurons were defined by morphology and by labeling with the TUJI antibody against β3 3-tubulin (Groves, A. K., et al., *Dev. Biol.*, 159:87–104 (1993); Moody, S. Q., et al., *J. Comp. Neurol.*, 279:567–580 (1989)) Cultures were in DMEM-BS. There was no BrdU labeling of neurons, nor was there any correlation between the extent of BrdU labeling in non-neuronal populations and the number of neurons present (data not shown). Analysis of DNA synthesis by BrdU incorporation (Gratzner, H. G., *Science*, 318:474–475 (1982)) confirmed that this increase in neuronal number was not due to cell division, strongly implicating differential cell death as the reason for the difference.

Values shown are means±DS for quadruplicate coverslips from the one of four experiments, all of which yielded similar results.

D. Response of kidney cells±NAC±EGF

Figure 7:
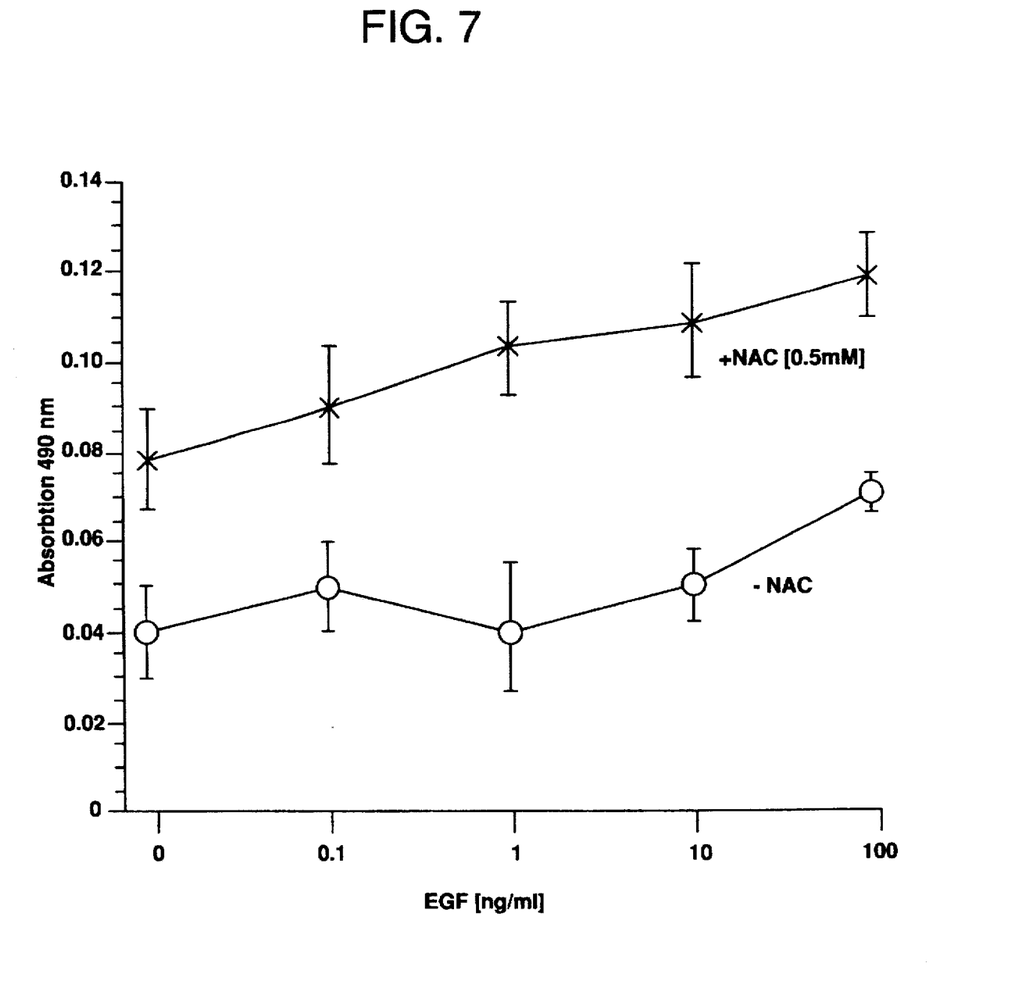
FIG. 7 shows the effects of NAC±EGF on kidney cells.

FIG. 7 was analyzed as for FIG. 1(B), but used embryonic kidney cells. There was no TNF exposure. The cells grown in the 96-well trays were derived by dissociation of kidney rudiments from 11 day embryonic rats. Cells were grown in DMEM-BS±epidermal growth factor (at the concentrations indicated)±NAC. The figure demonstrates that at all concentrations of EGF examined, cultures exposed to the EGF+NAC contained more cells than cultures exposed to EGF-NAC.

E. The Effect of NAC and PDGF on the Generation of Precursor Cells and Their Differentiated Progeny.

The effect of NAC on generation of O-2A progenitors and oligodendrocytes was examined in cultures of purified O-2A progenitors (prepared as in Example IA) exposed to platelet-derived growth factor (PDGF), the best-characterized mitogen for O-2A progenitor cells. Cells in these cultures were exposed to the indicated amounts of PDGF, and cultures were scored for the total numbers scored for the total numbers of oligodendrocytes and progenitors (as determined by labeling with) anti-GalC and A2B5 antibodies, as in Mayer et al., *Glia* 8:12–19 (1993). The data demonstrates that the addition of 1 mM NAC to these cultures is associated with a marked increase in the numbers of both progenitors and oligodendrocytes present in the cultures.

| Amount of PDGF | oligos | progenitors |
| --- | --- | --- |
| −NAC | | |
| 10 ng/ml | 134 + 15 | 227 + 37 |
| 1 ng/ml | 147 + 28 | 125 + 33 |
| 0.1 ng/ml | 199 + 38 | 16 + 8 |
| +NAC | | |
| 10 ng/ml | 331 + 85 | 834 + 90 |
| 1 ng/ml | 476 + 39 | 626 + 150 |
| 0.1 ng/ml | 339 + 160 | 239 + 33 |

F. Rescue of Oligodendrocytes from Apoptosis by CNTF+Vitamin C

Cells were prepared as in Example I(A), except that the initial plating density was 1,000 cells/coverslip. After 3 days in DMEM-BS, the resulting cultures of pure oligodendrocytes were switched to DMEM alone containing 0.5 ng/ml CNTF (a concentration that did not significantly protect cells on its own; see FIG. 4(A)±Vitamin C. After 3 further days of in vitro growth, cultures were analyzed in the same manner as experiments examining oligodendrocyte death induced by exposure to toxic stimuli. (See Example II(B))

Figure 8A:
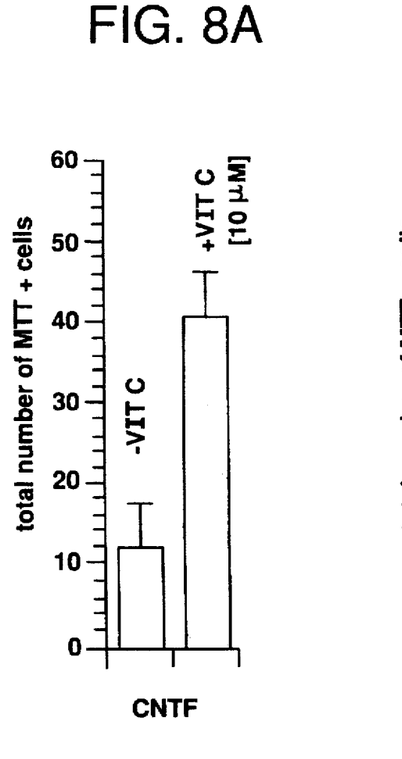
FIG. 8(a) shows the effects of vitamin C and CNTF on cells that would otherwise undergo apoptosis.
Figure 10:
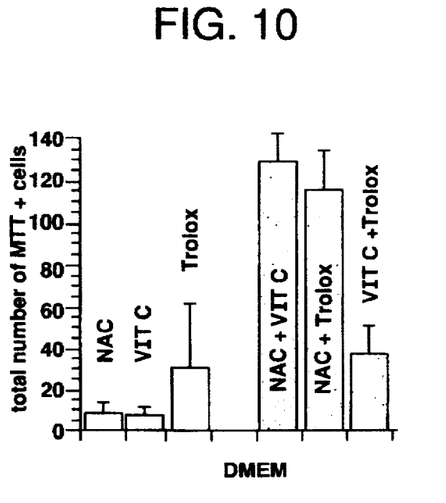
FIG. 10 shows the effects of NAC and trolox or vitamin C on cells that would otherwise undergo apoptosis.

As demonstrated in FIG. 8(a), the application of CNTF and Vitamin C together was associated with highly significant (**) increases in the extent of survival observed (see also FIG. 10. Values shown are means±SEM for quadruplicate coverslips from one of two experiments, both of which yielded similar results.

G. Rescue of Oligodendrocytes from Apoptosis by CNTF+Trolox

Cells were prepared as in Example I(A), except that the initial plating density was 2,000 cells/coverslip. After 3 days in DMEM-BS, the resulting cultures of pure oligodendrocytes were switched to DMEM alone to which was added 0.5 ng/ml CNTF±Trolox. After 3 further days of in vitro growth, cultures were analyzed in the same manner as experiments examining oligodendrocyte death induced by exposure to toxic stimuli. (See Example II(B))

Figure 8B:
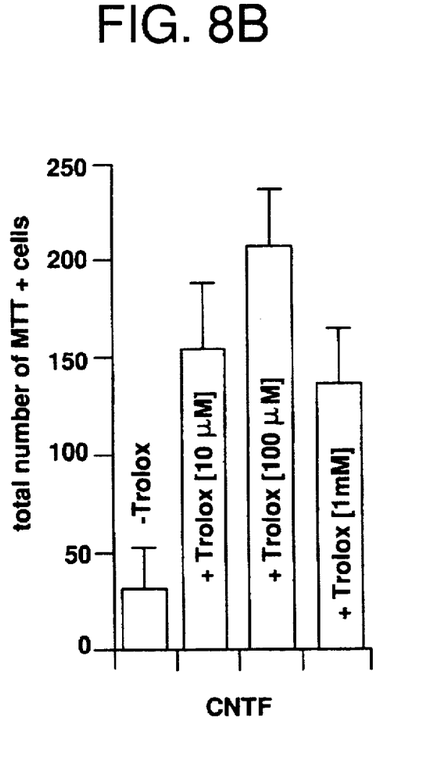
FIG. 8(B) shows the effects of trolox and CNTF on cells that would otherwise undergo apoptosis.

As demonstrated in FIG. 8(b), the application of CNTF and Trolox together was associated with highly significant (**) increases in the extent of survival observed (see also FIG. 10 and FIG. 4). Values shown are means±SEM for five coverslips from one experiment.

H. Rescue of Oligodendrocytes from Apoptosis by NAC+Progesterone

Figure 9:
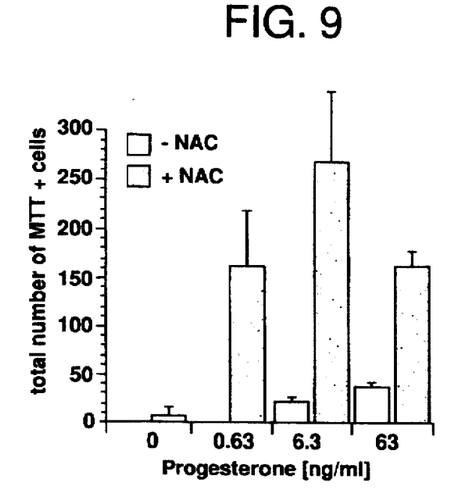
FIG. 9 shows the effects of progesterone and NAC on cells that would otherwise undergo apoptosis.

Cells were prepared as in Example I(A), except that the initial plating density was 2,500 cells/coverslip. After 3 days in DMEM-BS, the resulting cultures of pure oligodendrocytes were switched to DMEM alone to which was added progesterone±1 mM NAC (FIG. 9). After 3 further days of in vitro growth, cultures were analyzed in the same manner as experiments examining oligodendrocyte death induced by exposure to toxic stimuli. (See Example II(B))

As demonstrated in FIG. 9, the presence of 1 mM NAC in combination with progesterone was associated with highly significant increases (**) in the extent of survival observed. Values shown are means±SEM for quadruplicate coverslips from one of two experiments, both of which yielded similar results.

I. Rescue of Oligodendrocytes from Apoptosis by (a) NAC+Trolox, (b) NAC+Vitamin C Cells were prepared as in Example I(A), except that the initial plating density was 2,500 cells/coverslip. After 3 days in DMEM-BS, the resulting cultures of pure oligodendrocytes were switched to DMEM alone to which was added 10 uM Vitamin C or 100 uM Trolox±1 mM NAC (FIG. 10). After 3 further days of in vitro growth, cultures were analyzed in the same manner as for experiments examining oligodendrocyte death induced by exposure to toxic stimuli. (See Example II(B))

As demonstrated in FIG. 10, no compound alone promoted significant cell survival, nor did the combination of Vitamin C with Trolox, but the presence of 1 mM NAC in combination with either Vitamin C or Trolox was associated with highly significant increases (**) in the extent of survival observed. Values shown are means±SEM for quadruplicate coverslips from one three experiments, all of which yielded similar results.

J. Rescue of Oligodendrocytes from Apoptosis by (a) Progesterone+NAC+Trolox+Vitamin C, (b) CNTF+JGF-I+NT-3, (c) Progesterone+NAC+Trolox, and (d) Progesterone+NAC+Vitamin C Cells were prepared as in Example I(A), except that the initial plating density was 2,000 cells/coverslip. After 3 days in DMEM-BS, the resulting cultures of pure oligodendrocytes were switched to DMEM alone to which was added (a) progesterone (63 ug/ml)+NAC (1 mM)+trolox (100 uM)+Vitamin C (10 uM) ("combination 1") or (b) CNTF (10 ng/ml)+IGF-1 (50 ng/ml)+NT-3 (5 ng/ml) ("combination 2"). After 3 further days of in vitro growth, cultures were analyzed in the same manner as experiments examining oligodendrocyte death induced by exposure to toxic stimuli. (See Example II(B))

In all conditions, the 100% value corresponds to the cell survival seen in cultures of oligodendrocytes not subjected to trophic factor withdrawal.

|  | DMEM alone | Combination 1 | Combination 2 |
|---|---|---|---|
| Day 2 | 42 ± 17% | 81 ± 20% | 78 ± 19% |
| Day 3 | 14 ± 3% | 59 ± 10% | 80 ± 20% |
| Day 5 | 0 | 25 ± 8% | 11 ± 3% |

As the data shows, combination 1 was more effective at promoting long term cell survival than combination 2, a combination of RTK and RawTK agonists.

In other experiments, it was determined that Vitamin C can be removed from the combination of progesterone+NAC+Trolox+Vitamin C without loss of activity, and that the combination of progesterone+NAC+Vitamin C is more efficacious than either progesterone+NAC or progesterone+Vitamin C, although, as disclosed in Example III(H), these latter combinations are themselves effective.

K. Rescue of Oligodendrocytes from Apoptosis by (a) IGF-1+Vitamin C

Cells were prepared as in Example I(A), except that the initial plating density was 2,000 cells/coverslip. After 3 days in DMEM-BS, the resulting cultures of pure oligodendrocytes were switched to DMEM alone to which was added 1 ng/ml of IGF-1, 10 uM Vitamin C, or the combination 0.1 ng/ml of IGF-1+10 uM Vitamin C. After 3 further days of in vitro growth, cultures were analyzed in the same manner as for experiments examining oligodendrocyte death induced by exposure to toxic stimuli. (See Example II(B))

As shown in the following Table, the combination of Vitamin C with suboptimal doses of IGF-1 was associated with significant levels of oligodendrocyte survival.

| Condition | Survival (as % of DMEM-BS control) |
|---|---|
| IGF-I, 0.1 ng/ml | 1 ± 1 |
| IGF-I, 0.1 ng/ml + 10 uM Vit C | 41 ± 8 |
| 10 uM Vit C | 2 ± 3 |

L. Rescue of Oligodendrocytes from Apoptosis by (a) Progesterone+Vitamin C, (b) Progesterone+Trolox Cells were prepared as in Example I(A), except that the initial plating density was 2,000 cells/coverslip. After 3 days in DMEM-BS, the resulting cultures of pure oligodendrocytes were switched to DMEM alone to which was added progesterone, Trolox, Vitamin C, and NAC, and various combinations thereof. After 3 further days of in vitro growth, cultures were analyzed in the same manner as for experiments examining oligodendrocyte death induced by exposure to toxic stimuli. (See Example II(B))

As shown in the As shown in the Table, the combination of either of these antioxidants with progesterone was associated with significant levels of oligodendrocyte survival, a result not obtained when any of these compounds were used in isolation.

| Condition |  | Survival (as % of DMEM-BS control) |
|---|---|---|
| Progesterone | .63 ng/ml | 0 |
| Progesterone | 6.3 ng/ml | 4 ± 1 |
| Progesterone | .63 ng/ml + Vit C 10 uM | 21 ± 6 |
| Progesterone | 6.3 ng/ml + Vit C 10 uM | 28 ± 4 |
| Progesterone | .63 ng/ml + Trolox 100 uM | 27 ± 2 |
| Progesterone | 6.3 ng/ml + Trolox 100 uM | 24 ± 9 |
| Trolox | 100 uM | 6 ± 5 |
| Vit C | 10 uM | 1 ± 1 |
| NAC | 1 mM | 2 ± 1 |

EXAMPLE IV

Response of Oligodendrocytes to Complement±NAC

Pure cultures of oligodendrocytes were prepared as in Example IA. Half of the cultures were incubated with 1 mM NAC for 24 hours, while half were maintained in chemically defined medium. At the end of this time, rabbit complement (purchased from Buxted) was added for 1 hour at the indicated concentrations, washed out, and then cultures were analyzed under a microscope for the number of surviving cells. Morphological analysis of survival was confirmed by MTT staining, as in previous examples, and average numbers of surviving cells/coverslip are shown. The data shown indicates that NAC is an extremely potent protector against delayed-stage killing by complement (i.e., killing at lower complement concentrations) and also can confer some protection against complement-mediated killing at concentrations that are rapidly lethal.

|  |  | Number of Cells | |
|---|---|---|---|
| Complement Dilution | Time of Assay | –NAC | ±NAC |
| no complement | 1 hr | 418 | 427 |
| 1:8 | 1 hr | 1 | 42 |
| 1:11 | 1 hr | 3 | 216 |
| 1:21 | 1 hr | 244 | 439 |
| no complement | 24 hr | 298 | 374 |
| 1:8 | 24 hr | 0 | 80 |
| 1:11 | 24 hr | 0 | 252 |
| 1:21 | 24 hr | 110 | 318 |

EXAMPLE V

Treatment of MS patient with NAC

A patient in the advanced stages of MS was treated with NAC. The patient had little or no use of her legs, restricted use of her arms, considerable tremor, and loss of vision. Her MRI scan showed, as expected, a considerable extent of inflammatory activity in the central nervous system, as defined by the presence of enhancing lesions. According to the patient's own testimony, she was always tired, was having further attacks with great frequency, and frequently suffered exacerbations if she became ill with other diseases, in particular chest infections. This is a typical situation for a patient in advanced stages of MS.

The patient began to take NAC, initially at oral doses of 600 mg/day and escalating to 1200 mg/day. Within several days of starting treatment, she felt less tired. She stopped relapsing, and even experienced several episodes of colds and chest infections without succumbing to another MS relapse. An MRI scan, taken two years after initiation of treatment with NAC, showed no signs of enhchancing lesions or other evidence of inflammatory activity in the CNS. Throughout this time, NAC was taken on a daily basis at doses of 600 mg or 1200 mg/day, dependent upon the patient's self-evaluation.

For an MS patient in such an advanced stage of disease to go for this length of time relapse-free, and to show no active lesions by MRI scanning is remarkable. This can only have been attributable to the treatment with NAC, as there were no other significant changes in the treatment of this patient, and no previous treatments had done anything to slow the course of disease.

What is claimed is:

1. A method for treating a disease or condition characterized by an insufficiency of a particular cell type or types and whose therapy comprises the administration of at least one growth factor selected from the group consisting of ciliary neurotropic factor (CNTF); insulin-like growth factor-I (IGF-I); nerve growth factor (NGF); epiderimal growth factor (EGF); interferon-gama (INF-gama); and platelet-derived growth factor said growth factor acting to promote the division, generation and/or survival of the particular cell type or cell types, said method comprising administering a therapeutically effective amount of said growth factor in combination with an agent capable of raising intracellular glutathoione levels.

2. A method according to claim 1 wherein said agent capable of raising intracellular glutathione levels is N-acetylcysteine (NAC).

3. A method according to claim 1 wherein said disease is amyotrophic lateral sclerosis (ALS), said growth factor is CNTF, and said agent capable of raising intracellular glutathione levels is N-acetylcysteine (NAC).

4. A method according to claim 1 wherein said disease is Parkinsons's said growth factor is nerve growth factor, and said agent capable of raising glutathione levels is NAC.

5. A method for treating a disease or condition characterized by an insufficiency of a particular cell type or types and whose therapy comprises the administration of ciliary neurotrophic factor (CNTF) to promote the survival of the particular cell type or cell types, said method comprising administering a therapeutically effective amount of said ciliary neurotrophic factor (CNTF) in combination with an agent selected from the group consisting of an agent that raises intracellular glutathione, vitamin C and trolox.

6. The method according to claim 5, wherein said disease or condition is amyotrophic lateral sclerosis.

7. The method according to claim 5, wherein said agent is trolox.

8. The method according to claim 5, wherein said agent is Vitamin C.

9. A method for treating a disease or condition characterized by an insufficiency of a particular cell type or types and whose therapy comprises the administration of insulin-like growth factor (IGF-1) to promote the survival of the particular cell type or cell types, the method comprising administering a therapeutically effective amount of insulin-like growth factor (IGF-1) in combination with an agent selected from the group consisting of an agent that raises intracellular glutathione, vitamin C or trolox.

10. The method according to claim 9, wherein said disease or condition is ALS.

11. The method according to claim 9, wherein said agent is trolox.

12. The method according to claim 9, wherein said agent is Vitamin C.

* * * * *